United States Patent [19]
Michael et al.

[11] Patent Number: 5,768,443
[45] Date of Patent: Jun. 16, 1998

[54] METHOD FOR COORDINATING MULTIPLE FIELDS OF VIEW IN MULTI-CAMERA

[75] Inventors: David Michael, Newton; Aaron Wallack, Natick, both of Mass.

[73] Assignee: Cognex Corporation, Natick, Mass.

[21] Appl. No.: 574,733

[22] Filed: Dec. 19, 1995

[51] Int. Cl.⁶ .................................................. G06K 9/32
[52] U.S. Cl. ........................................ 382/294; 382/151
[58] Field of Search ................................. 382/294, 151, 382/152, 284; 355/203; 348/159, 95

[56] References Cited

U.S. PATENT DOCUMENTS

| | | | |
|---|---|---|---|
| 4,847,911 | 7/1989 | Morimoto et al. | 382/151 |
| 5,145,432 | 9/1992 | Midland et al. | 348/95 |
| 5,325,443 | 6/1994 | Beatty et al. | 382/152 |
| 5,528,290 | 6/1996 | Saund | 382/284 |
| 5,542,002 | 7/1996 | Choate et al. | 382/287 |
| 5,611,000 | 3/1997 | Szeliski et al. | 382/294 |

*Primary Examiner*—Yon J. Couso
*Attorney, Agent, or Firm*—Russ Weinzimmer

[57] ABSTRACT

A method is provided for use in a multi-camera machine vision system wherein each of a plurality of cameras simultaneously acquires an image of a different portion of an object of interest. The invention makes it possible to precisely coordinate the fields of view of the plurality of cameras so that accurate measurements can be precisely performed across multiple fields of view, even in the presence of image distortion within each field of view. The method includes the steps of, at calibration-time, fixing the plurality of cameras with respect to a substantially rigid dimensionally-stable substrate including a plurality of calibration targets each having a reference feature. For each camera, an image of a calibration target is acquired to provide a plurality of acquired calibration target images. Then a distortion-correction map is generated for each acquired calibration target image. At run-time, for each camera, an image is acquired, at least two of the images including a portion of the object to provide a plurality of partial object images. These partial object images are then transformed by a distortion-correction map to provide a plurality of corrected partial object images. Next, relative displacement information is used to determine the relative displacement of a first point in a first corrected partial object image with respect to a second point in a second corrected partial object image. A combined map can be generated that both corrects image distortion, and transforms local camera coordinates into global coordinates.

20 Claims, 8 Drawing Sheets

METHOD FOR COORDINATING MULTIPLE FIELDS OF VIEW IN MULTI-CAMERA

FIELD OF THE INVENTION

This invention relates generally to machine vision, and particularly to machine vision systems having multiple cameras.

BACKGROUND OF THE INVENTION

Machine vision systems having multiple cameras are known. It is also known to simultaneously acquire images from each of a plurality of cameras in a machine vision system. Machine vision systems having a single camera for semiconductor wafer inspection, guidance, gauging, and location are also known. However, presently, it is not possible to precisely coordinate the fields of view of the plurality of cameras so that measurements can be performed across multiple fields of view to a precision of fractions of a millimeter, especially when there is significant image distortion in each field of view.

In most machine vision applications where the object of interest is a semiconductor wafer, or portion thereof, a single standard-resolution camera provides adequate resolution and scene area coverage. In such applications where higher resolution is needed, magnifying optics can be used, but scene area coverage is reduced. Alternatively, a higher-resolution camera can be used, thereby preserving scene area coverage, but such cameras can be prohibitively expensive, or unavailable at the resolution required by the application.

Resolution is defined as the number of pixels that correspond to each unit area in a physical scene. Thus, resolution determines how much scene area can be represented by each pixel of an image provided by a vision camera. A high resolution camera allocates a large number pixels to each unit area. Thus, each pixel of an image provided by a high-resolution camera represents a smaller portion of the physical scene than each pixel of an image provided by a low-resolution camera, assuming that both cameras are equipped with the same optics and are located at the same position.

In some machine vision applications, both high resolution and coverage of widely separated portions of a large scene are simultaneously required. It is clear that one solution to the problem of achieving high resolution images of a scene area greater than can be covered by a single camera is to use more than one camera, each camera having a field-of-view that covers only a portion of the scene area.

However, when there is more than one field of view, the relative physical positions of the respective reference origins of the fields of view are inherently indeterminate without reference to a common coordinate system. Consequently, position information in the image from each field of view cannot be related to position information from the other fields of view. Therefore, information interrelating the coordinate systems of multiple fields of view must somehow be provided.

Although such information can be obtained visually, by capturing in each field of view an image of a landmark disposed at a known position in relation to a common coordinate system, position information so-obtained in a machine vision system may not be sufficiently precise for many applications. This is due to lens-related and camera-related distortion effects. Unfortunately, attempting to correct these distortion effects may degrade the final accuracy of the visually acquired landmark position information relative to the common coordinate system.

SUMMARY OF THE INVENTION

A method is provided for use in a multi-camera machine vision system wherein each of a plurality of cameras simultaneously acquires an image of a different portion of an object of interest. The method of the invention makes it possible to precisely coordinate the fields of view of the plurality of cameras so that accurate measurements can be performed across multiple fields of view to a precision of fractions of a millimeter. The invention provides both high resolution, and coverage of widely separated portions of a large scene. The invention exploits a common coordinate system when there is more than one field of view, allowing position information from each field of view to be related to position information from the other fields of view. In addition, the invention provides information interrelating the coordinate systems of multiple fields of view, with improved precision that facilitates use in many applications, without loss of accuracy due to image distortion effects.

According to the invention, a method is provided both for coordinating multiple fields of view of a plurality of cameras so as to facilitate determining the distance between features each disposed within a different field of view, and for correcting image distortion in each field of view. The method includes the steps of, at calibration-time, fixing the plurality of cameras with respect to a substantially rigid dimensionally-stable substrate, such as a plate, including a plurality of calibration targets each having a reference feature, such that a calibration target is within the field of view of each camera. Relative displacement information is acquired regarding at least the linear displacement of each reference feature with respect to at least one other reference feature. For each camera, an image of a calibration target is acquired to provide a plurality of acquired calibration target images. Then a distortion-correction map is generated for each acquired calibration target image.

At run-time, an object to be viewed is rigidly mounted such that a portion of the object is within the field of view of at least two cameras. Then, for each camera, an image is acquired, at least two of the images including a portion of the object to provide a plurality of partial object images. These partial object images are then transformed by a distortion-correction map to provide a plurality of corrected partial object images. Next, the relative displacement information is used to determine the relative displacement of a first point in a first corrected partial object image with respect to a second point in a second corrected partial object image. In a preferred embodiment, the step of generating a distortion-correction map includes the step of determining the coefficients of a polynomial. Preferably, the polynomial is a fifth-order polynomial. For greater computational efficiency without sacrificing accuracy, it is preferred to generate a distortion correction map by pre-computing the map and storing the results in a look-up table. According to the invention a combined map can be generated that both corrects image distortion, and transforms local camera coordinates into global coordinates.

BRIEF DESCRIPTION OF THE DRAWINGS

The invention will be more fully understood from the following detailed description, in conjunction with the accompanying figures, wherein.

DETAILED DESCRIPTION OF THE PREFERRED EMBODIMENTS

Figure 1:
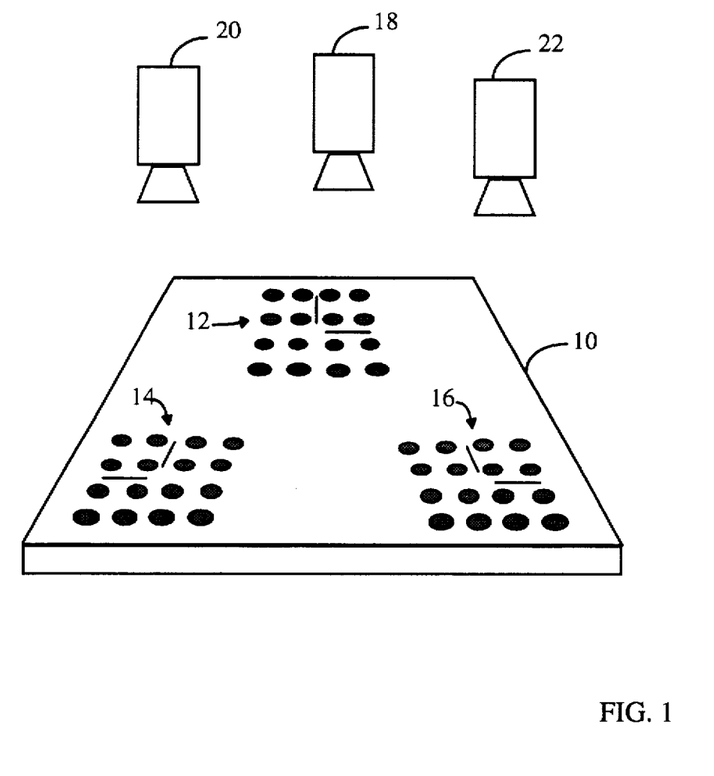
FIG. 1 is a schematic perspective representation of the calibration apparatus for use with the invention.

FIG. 1 provides a schematic perspective of an embodiment of the calibration substrate for use with the invention. In this instance, the substrate is in the form of a rectangular plate 10 having three calibration targets 12, 14, 16, disposed so as to facilitate viewing by three cameras 18, 20, 22, respectively. Calibration targets can be rotated with respect to each other calibration target, and cameras can be rotated with respect to each other camera.

A calibration target can be rotated at any angle with respect to an axis of maximum resolution of a camera, but improved performance in some applications can be achieved by aligning a non-diagonal symmetry axis of a calibration target with the axis of maximum resolution of a camera. For example, if a camera has rectangular pixels, the axis of maximum resolution is perpendicular to the longitudinal axis of each rectangular pixel. When the feature of interest is the perimeter of a semiconductor wafer, its radial position can be most accurately measured by orienting the field of view of the camera so that the axis of maximum resolution of the camera is perpendicular to a tangent to the wafer perimeter.

The substrate should be rigid, especially when the lens used in the machine vision cameras is not telecentric, and so would not provide an orthographic projection. It is even more important that the substrate be dimensionally stable, so as to ensure that the distances between and within calibration targets remains substantially constant. For example, the substrate should be made from a material that has well understood thermal expansion properties. Likewise, the substrate should not be made from an elastic material. Examples of suitable materials include glass, transparent crystal, metal, and silicon.

To facilitate handling with a vacuum chuck, to rigidly mount the substrate, for example, the underside of the plate 10 is substantially smooth. The substrate can be rigidly mounted in other ways, such as using a vice, or a pneumatic toe clamp.

Figure 5:
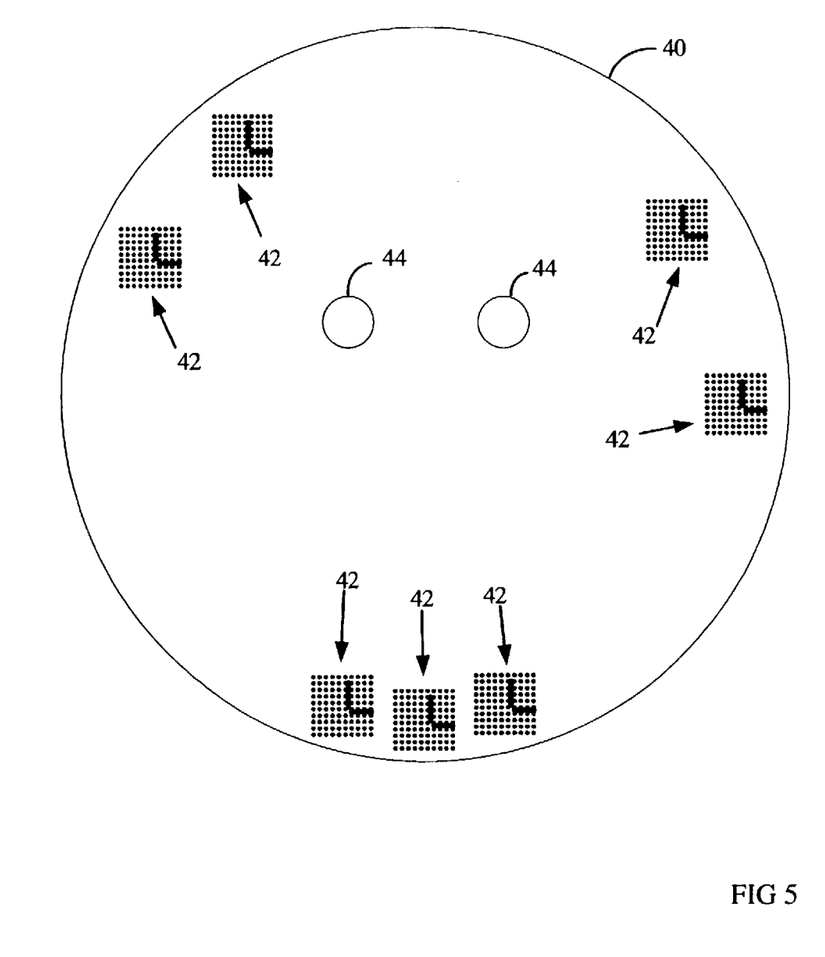
FIG. 5 is an embodiment for use with the invention having seven calibration targets disposed at seven possible camera locations, and a pair of holes for receiving a pair of dowel pins.

The number of calibration targets on the substrate is determined by the number of possible camera locations that may be used during the run-time phase, i.e., when the method of invention is actually used. For example, there may be three or four cameras, and a set of seven possible locations for each of the three or four cameras, requiring a calibration substrate having a calibration target at each of seven positions on the plate 40, as shown in FIG. 5.

In general, there can be as many calibration targets on a substrate as the surface area allows. Each calibration target is disposed at a position on the surface so as to facilitate direct viewing by a camera. In some applications, it may be advantageous for the substrate to include a regular array of calibration targets having systematic inter-target spacing.

Figure 4:
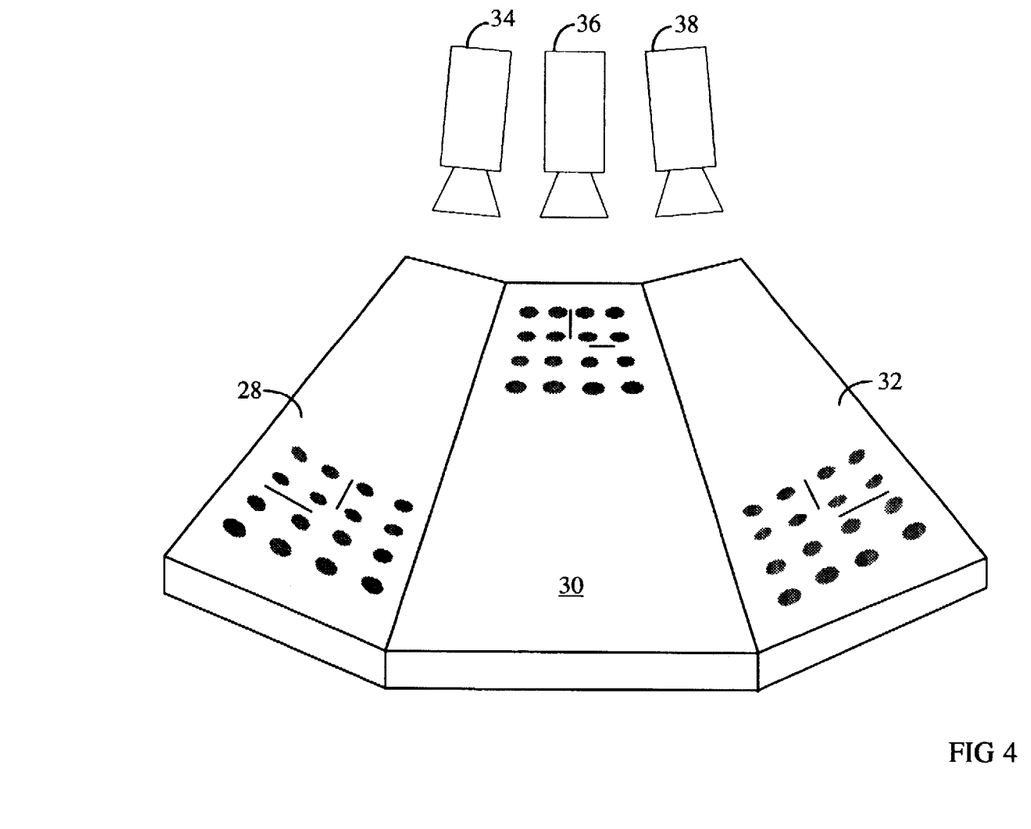
FIG. 4 is a substrate having a plurality of non-coplanar planes; one plane for each camera.

In a preferred embodiment, each camera views the calibration target such that the central axis of the camera lens system is co-linear to the normal direction at the center of the calibration target, i.e., perpendicular to the plane of the calibration target, as shown, for example, in FIG. 4. It should be noted that if the cameras are mounted to a material with thermal expansion properties, temperature can affect the position of each camera with respect to the substrate, and therefore must be taken into account, as is well understood by those skilled in the art.

Figure 2:
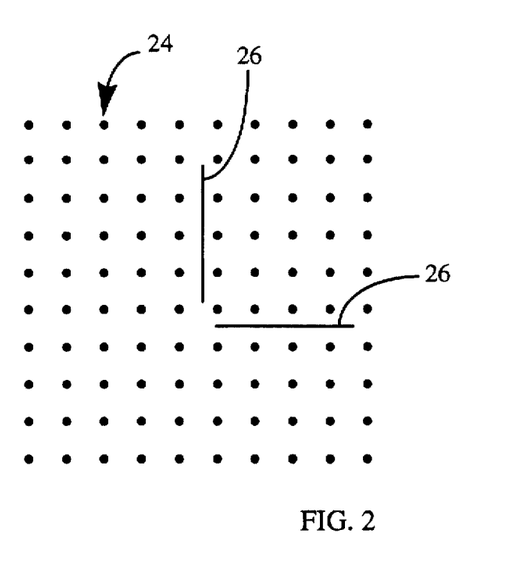
FIG. 2 is a representation of a calibration target having a regular array of dots for use in camera distortion correction, and a pair of non-parallel lines for use as a position-determination "landmark"
Figure 2A:
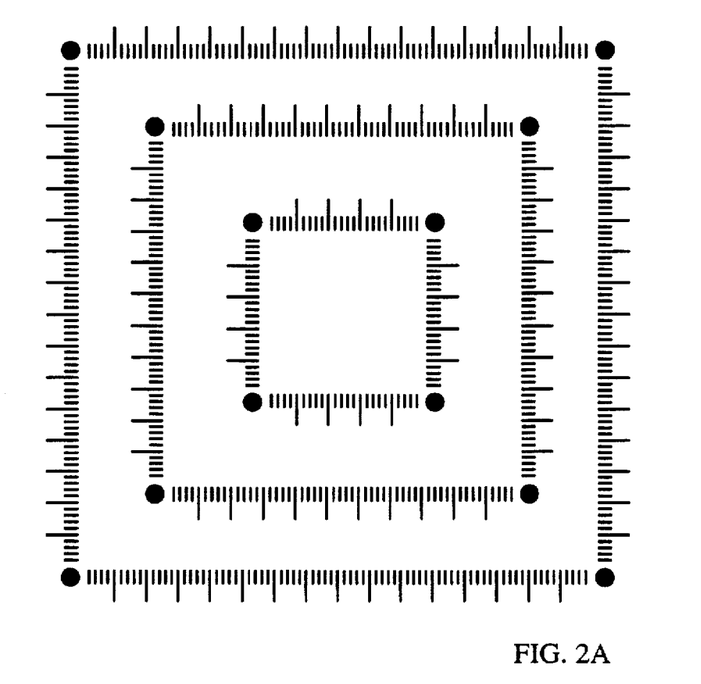
FIG. 2A is a representation of a calibration target having a combination of scales and dots.

With reference to FIG. 2, each of the calibration targets 12, 14, 16 shown in FIG. 1 includes a regular array of dots 24 for use in camera distortion correction, and a pair of non-parallel lines 26 for use as a position-determination "landmark". Preferably, the pair of non-parallel lines is mutually perpendicular. Alternatively, a combination of scales and dots can be used, as shown in FIG. 2A. Advantageously, a "checkerboard" pattern, such as alternating black and white, or grey and white squares can be used. In general, any graphical design that provides a regular array of features can be used as a calibration target.

Alternatively, each calibration target includes relative position and orientation information, such as the position and orientation of the calibration target with respect to at least one other calibration target, or with respect to an origin anywhere on the substrate. Alternatively, each calibration target can include an index value that leads to relative position and orientation information stored elsewhere. The relative position and orientation information is advantageously encoded in a manner that enhances machine-readability, such as a 1-D or 2-D "barcode", or simply presented in a machine-readable font.

Alternatively, a single calibration target covers the entire surface area of the substrate, portions of which are used by each camera, including multiple instantiations of a "landmark", each landmark being disposed at a possible camera location. To anticipate most possible camera locations, a regular array of landmarks can be included. In another version of this alternate embodiment, each landmark includes relative position and orientation information that provides position and orientation information relative to at least one other landmark or to an origin point, or includes an index value leading to relative position information stored elsewhere. The position and orientation information is advantageously encoded so as to optimize machine readability, such as by using a 1-D or 2-D "barcode", or simply presented in a machine-readable font.

Figure 3:
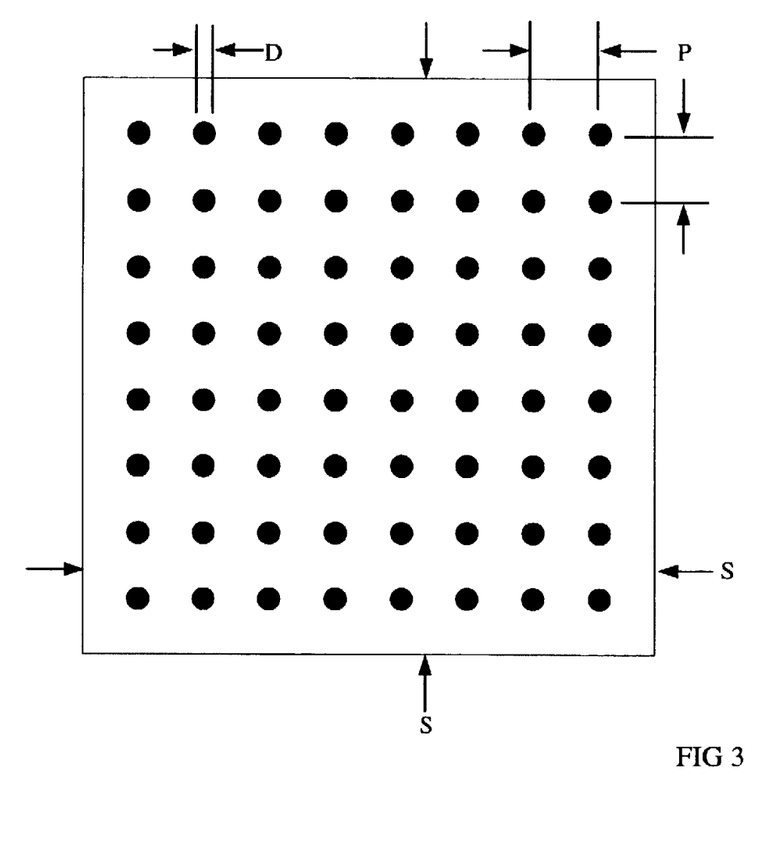
FIG. 3 is a calibration target that includes a square array of dots, characterized by the parameters $D_x$, $P_x$, $S_x$, $D_y$, $P_y$, and $S_y$.

FIG. 3 shows a calibration target that primarily includes a square array of dots, characterized by the parameters $N_X$, $N_Y$, D, P, and S. Here, $N_X$ is the number of dots along the X-axis, $N_Y$ is the number of dots along the Y-axis, D is the diameter of each dot, P is the pitch or spacing of the array of dots, and S is the size of the area covered by the dots. In most applications $N_X$ is equal to $N_Y$. For example, to locate the position and orientation of an object having a boundary that traverses the field of view of a plurality of cameras, the values of $N_x$, $N_y$, D, P, and S can advantageously be about 20 dots, 20 dots, 15 pixels, 30 pixels, and 600 pixels, respectively. Many vendors can manufacture a plate having a plurality of such calibration targets, such as Max Levy Autograph, Inc., Philadelphia, Pa., and Applied Image Corporation, Rochester, N.Y. It is possible to manufacture a plate having calibration targets where the maximum dot location error is on the order of one micron.

Referring again to FIG. 2, a calibration target as included in the invention can also include a "landmark". According to the invention, a landmark is a feature of a calibration target characterized by a known position with respect to at least one other landmark. Thus, knowing the position of an image feature with respect to a first landmark can, in combination with knowledge of the distance between the first landmark and a second landmark, provide knowledge of the position of the image feature with respect to the second landmark.

Further, knowledge of the distance of a landmark with respect to an origin of a global reference frame that includes a plurality of fields of view can, in combination with knowledge of the distance between the landmark and an image feature, provide the coordinates of the image feature in the global reference frame, regardless of which field of view includes the image feature.

For example, a pair of perpendicular lines 26 can be used as a "landmark". Alternatively, any other graphical feature that specifies a point in a calibration target can serve as a landmark, such as a pair of non-parallel lines, a cross-hair, or a bull's-eye, for example. It is also possible to use a group of dots, or other portion of a calibration target as a landmark. For example, the lower left dot, or lower left square grouping of four dots, can also serve as a landmark. Also, a missing dot in an otherwise regular array of dots can serve as a landmark.

Although FIG. 1 shows a substrate that is in the form of a rectangular plate 10 having three calibration targets 12, 14, 16, the substrate of the invention can take many other forms. For example, the substrate can include a plurality of non-coplanar planes; one plane for each camera, as shown in FIG. 4. In this case, each of the three planes 28, 30, 32 can include a plurality of calibration targets, or can include a single calibration target that covers a substantial portion of each plane. Although only a single camera is oriented towards each of the planes, more than one camera can be used in conjunction with each of the planes 28, 30, 32.

The substrate of the invention can also be a substantially circular plate, as shown in FIG. 5. The circular plate 40 can advantageously be sized so as to resemble a semiconductor wafer, for example. The plate 40 has six calibration targets 42 disposed at six possible camera locations.

In addition, the plate 42 includes two dowel pin holes 44 that can be used to repeatably fix the plate 40 with respect to the coordinate frame of a mechanical device, such as a wafer aligner. Given the position of a pair of dowel pins that are rigidly affixed to the mechanical device, one can then know positions of image points with respect to the coordinate frame of the mechanical device. As an alternative to the holes 44, the circular plate 40 can include a notch or flat in its perimeter, instead of the holes 44, the notch or flat being cooperative with contacting pins of the mechanical device.

Note that the invention does not require fixation of the substrate with respect to the coordinate frame of a mechanical device, such as a "wafer stepper" for performing the step-and-repeat operations of semiconductor device fabrication. However, in some applications, such fixation may provide additional benefits.

How To Use The Invention

Figure 6:
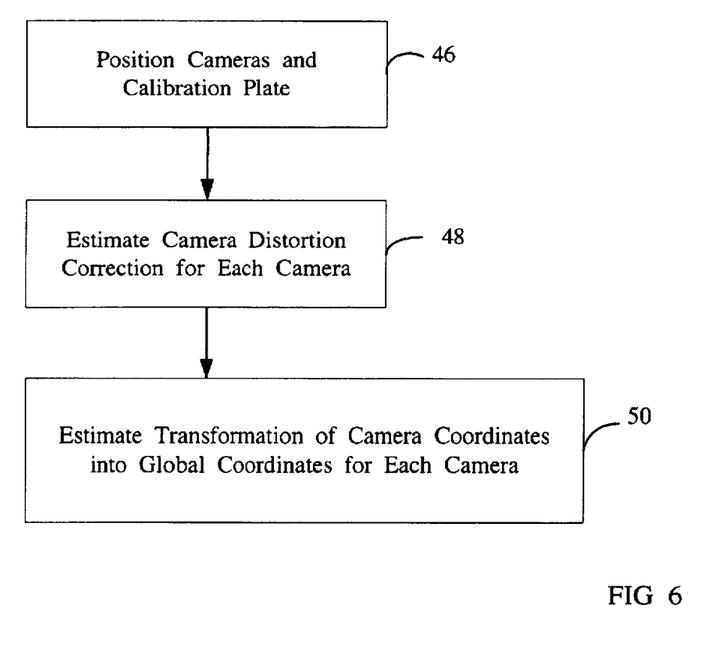
FIG. 6 is a flow chart illustrating the major steps of the calibration phase of the method of the invention.
Figure 9:
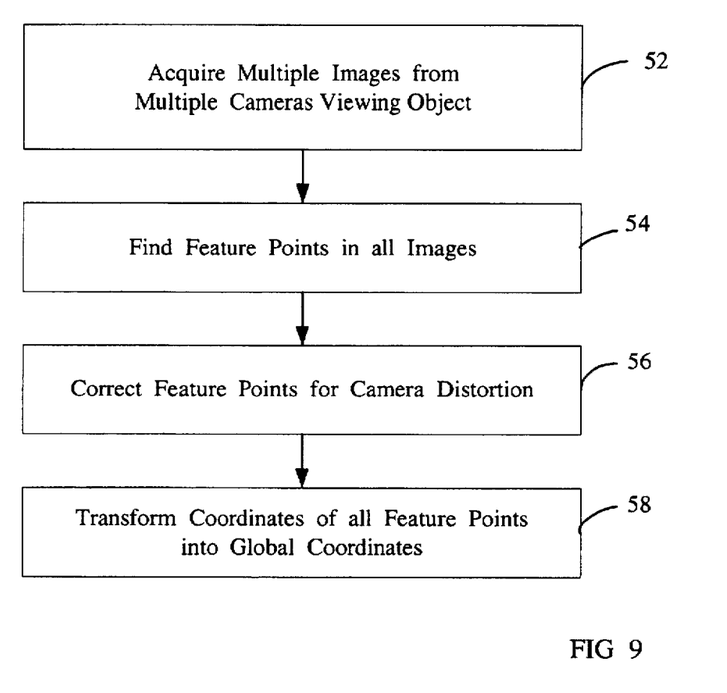
FIG. 9 is a flow chart illustrating the major steps of the run-time phase of the method of the invention.

The method of the invention can be used to determine the relative displacement of a first point in a first corrected field of view with respect to a second point in a second corrected field of view. The invention includes a calibration phase, as shown in FIG. 6, and a run-time phase, as shown in FIG. 9. Note that method steps are indicated in the text below by enclosure in parentheses.

Referring to FIGS. 1 and 6, the calibration phase of the invention includes the step (46) of positioning the cameras 18, 20, and 22 in fixed and rigid relationship with the calibration plate 10, such that a calibration target 12, 14, or 16 falls within the field of view of each camera 18, 20, and 22. The calibration plate 10 can be supported by an X-Y-Θ motion stage that can precisely translate and rotate the plate 10, and can even be secured to the motion stage using a vacuum chuck for enhanced stability. The X-Y-Θ motion stage can be controlled so as to bring the plate 10 into correct position with respect to the cameras 18, 20, and 22.

Next, a distortion correction map must be estimated (48) for each camera 18, 20, and 22. First, each camera 18, 20, and 22 acquires an image of a calibration target, such as a target as shown in FIG. 2. This calibration target includes a plurality of regularly spaced dots 26. Since it is known that the spacing of the dots 26 is regular, any departures from regularity evidenced by the acquired image of the dots represents distortion in some aspect of the image capture process. This distortion can be due to a variety of factors, to be discussed below. The distortion map can also compensate for translation and rotation of the acquired image of the calibration target with respect to a desired location and orientation of the calibration target in the field of view.

Image distortion in the acquired image can be due to one or more of the following factors: lens irregularities, such as astigmatism and coma; tilt of the lens in either the X- or Y-axis with respect to the plane of the imaging device, such as a CCD (charge coupled device); and tilt of the camera in either the X- or Y-axis with respect to the plane of the calibration target. Other types of image distortion include: perspective distortion, chromatic distortion, and many other types of distortion, as discussed in "Optics" by Hecht & Zajac, pp. 175–194, Copyright 1974, Addison-Wesley Publishing Company, Reading Mass. Also, normal lens behavior inevitably introduces some degree of image distortion.

Further, the distortion map can account for scale factors, such as the magnification of the camera lens system, and the image pixel-to-physical distance conversion, i.e., the amount of actual surface area of the physical image plane that is represented by each pixel in a particular camera's field of view.

Figure 7A:
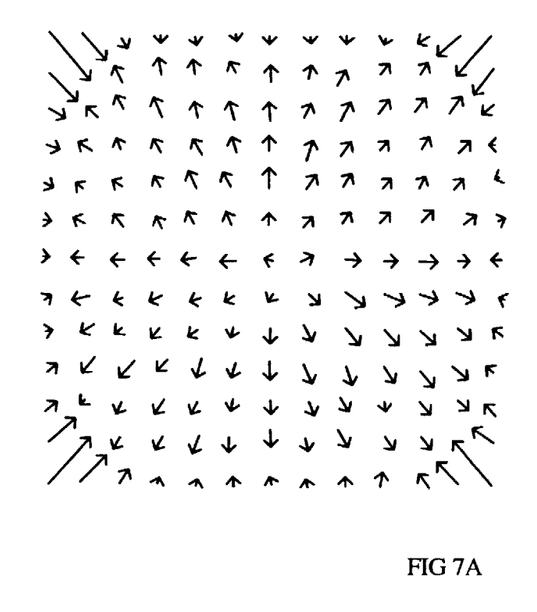
FIG. 7A is an error vector field of radially symmetric image distortion of an image, each error vector representing the distortion effect at the coordinates of the origin of the vector.
Figure 7B:
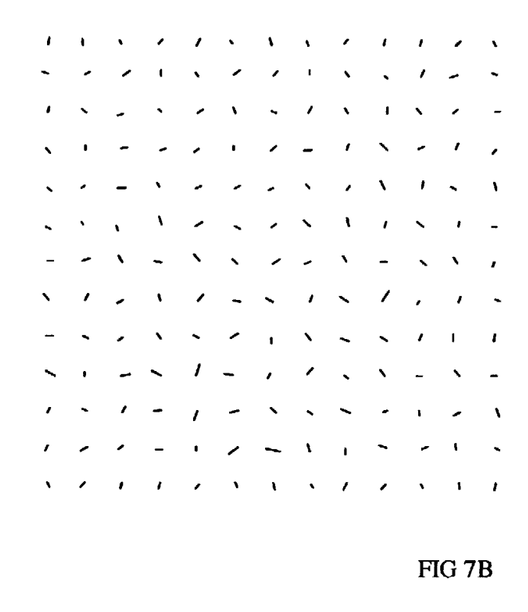
FIG. 7B is an error vector field of the image of FIG. 7A, after image distortion correction.

Referring to FIGS. 7A and 7B, one way to visualize the effects of image distortion in a single field of view is to plot the displacement of each dot of a calibration target, such as shown in FIG. 2, from its ideal position. For each dot in a field of view, there can be a displacement due to image distortion that is represented as a vector having a magnitude and a direction, and originating from an ideal dot position. Such a representation of a plurality of displacements, one displacement vector for each dot of a calibration target, is shown in FIG. 7A.

An image distortion correction map is a transformation that operates upon a distorted image so as to provide an undistorted image, i.e., to correct the distorted image. Thus, an image distortion correction map that would correct the image distortion shown in FIG. 7A is effectively the inverse of the map of FIG. 7A. When such a distortion correction map operates upon a distorted image of a calibration target, the result is substantially similar to the ideal image of the calibration target. FIG. 7B shows the small remaining deviations from ideal, as indicated by an array of short vectors, each of which looks like a dash oriented at an angle ranging from 0° to 360°.

In more formal terms, a distortion correction map is a function that transforms acquired image coordinates into corrected physical coordinates. The calibration target is used to establish a uniform distance metric for determining a corrected physical coordinate system, and the landmark feature of the calibration target is used to establish a local origin for the corrected physical coordinate system.

According to the invention, in the context of multiple fields of view, a distortion correction map is a function that transforms image coordinates in a particular field of view to the corrected local physical coordinates that correspond to that field of view. There can be a different distortion correction map for each camera of a multi-camera system. Then, to obtain the corrected local physical coordinates in a global physical reference frame that includes each field of view from all of the cameras, each set of corrected local physical coordinates must be transformed into global physical coordinates. According to the invention, there is a specific local-to-global coordinate transformation for the field of view of each camera, which transformation is estimated in step (50) of FIG. 6.

It is possible to generate a composite transformation that achieves the equivalent of an image correction transform followed by a local-to-global coordinate transform for each field of view in a multi-camera system. Thus, given local pixel coordinate data within a field of view, and an associated camera index value, a single transform can be obtained that provides global physical coordinate data, while also correcting image distortion.

Returning to FIG. 6, to estimate an image correction calibration map for a particular camera (48), a least-squares-fit of two corresponding sets of points is performed, which will now be described in detail.

A calibration map is a function that transforms image coordinates to corrected physical coordinates. Let's state this more precisely and formally. Call a point in image coordinates $\{u,v\}$, and a point in physical space $\{x,y\}$. Then a calibration map is a vector function F:

$$\{x,y\}=F(\{u,v\}) \tag{1}$$

This function can be represented by two real-valued functions:

$$x=G_x(u,v)$$

$$y=G_y(u,v) \tag{2}$$

How do we determine (i.e., compute) $G_x$ and $G_y$? First, we decide on the form of the functions themselves. That is:

$$G_x=G_x(a_i) \tag{3}$$

for some (potentially large) set of parameters $a_i$. $G_x$ can be a polynomial, an enormous lookup table, or a neural network!

Once we decide on the form, computing the map is reduced to finding the parameters $a_i$ that control the behavior of the map. Typically this is done by assembling a set of corresponding points that represent examples of what we want the map to compute. In other words, we produce sets of corresponding points for which we desire these maps:

$$x_i=G_x(u_i,v_i)$$

$$y_i=G_y(u_i,v_i) \tag{4}$$

Computing the map is often called fitting, because our map usually represents some kind of best fit between the coordinate sets $\{u_i,v_i\}$ and $\{x_i,y_i\}$. The computational task is simply this: given the sets of coordinates, compute the mapping parameters $a_i$.

The central difficulty of the fitting task is that we want the map to be an excellent fit between all points within the image and physical points that correspond to them, not just the small subset we've actually measured. We achieve this goal by choosing an appropriate form for the mapping function, and carefully selecting and measuring the subset of calibration points, or features.

There are two basic approaches to the nonlinear calibration mapping function, fitted function and grid interpolation. In the first approach we have a function $$\{x',y'\}=F(x,y) \tag{5}$$

that can achieve an acceptable fit for the type of distortion encountered. In other words, $$(\text{Error}=\|\{x',y'\}-F(x,y)\|)<\epsilon \tag{6}$$

for all points in the image, and $\epsilon$ is sufficiently small. You then find the coefficients of F via least-squares fitting.

The grid interpolation approach is to subdivide the image into small regions; in each region a correction is applied. The correction in one region has no particular relationship to a correction applied elsewhere in the image.

Grid interpolation has the advantage that any type of distortion can be corrected; you don't have to find a function whose symbolic form happens to form a good map. The closed-form approach can be more accurate because it will not be so influenced by measurement error; an incorrect grid point location can distort a region of the image.

Here are some ways of implementing an interpolation map:

GCL (General Calibration) (COGNEX VISION TOOL) computes a grid of linear transforms, each of which is applied to its local patch. The borders of the regions are triangular. The transforms are adjusted so the overall map is continuous across patch boundaries.

Bilinear interpolation of error vectors. Fit a linear transform to the calibration grid data. Find residual vectors from the grid. Store the vectors in a look-up table. Do bilinear interpolation on the grid to do complete correction. Use the bare linear transform for pre-lead-measurement inspection tasks.

Splined interpolation of error vectors, using bicubic splines, Coons patches, etc. This results in a smoother (but not necessarily more accurate) map than the bilinear interpolation.

Figure 8:
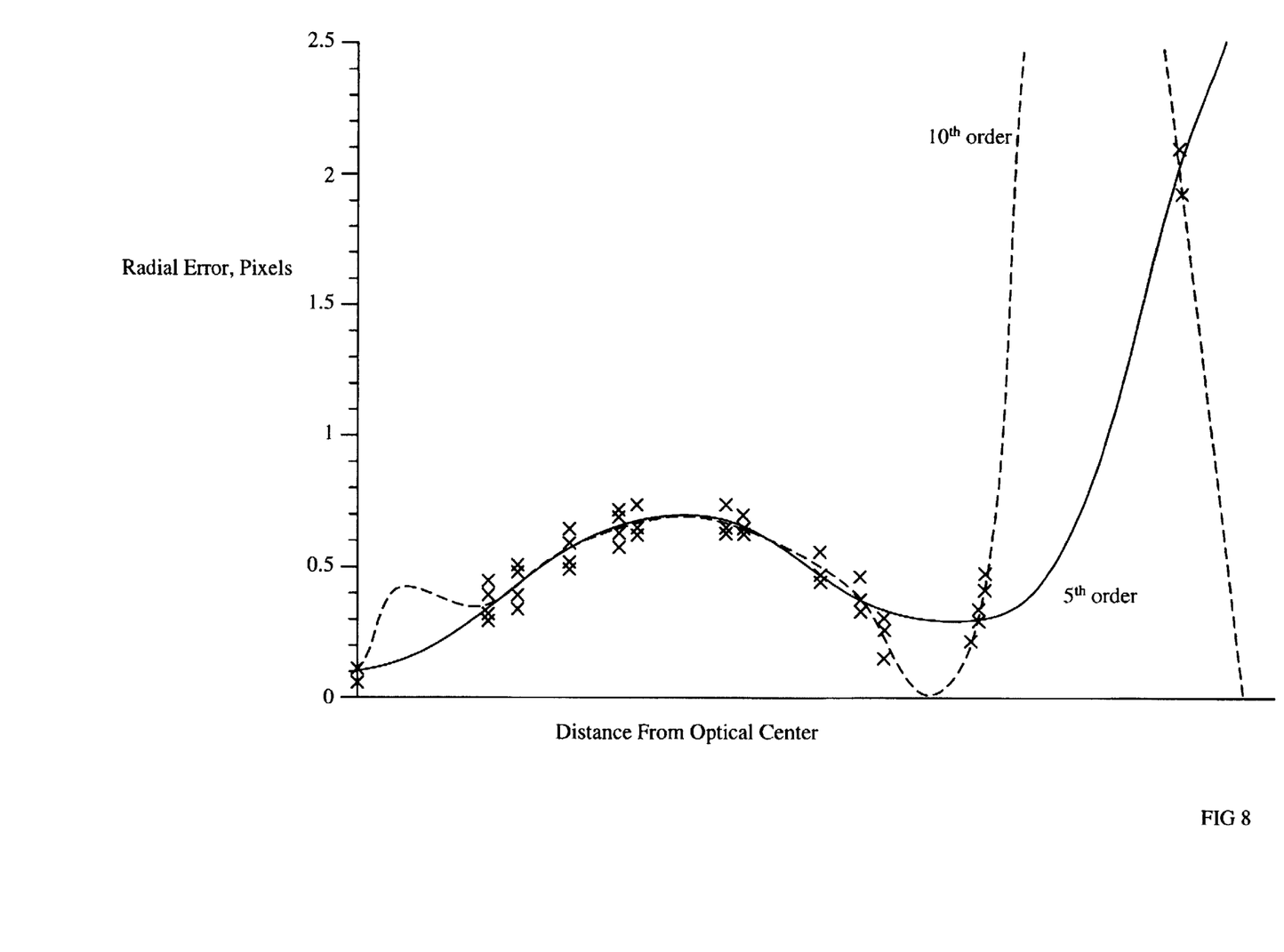
FIG. 8 is a plot of two different polynomial fits through eight radial sections of the error vector field of FIG. 7A.

Here are some ways of implementing a fitted function map:

Radial fit function to error vectors. For the uncorrected image in FIG. 7, note that the errors are predominantly radial in nature, around the optical center. Fit a polynomial or other closed-form function to the data This avoids the interpolation problems, and gives a differentiable (smoother) map. This only works for certain kinds of distortion, such as that seen in FIG. 7. FIG. 8 shows two different polynomial fits through 8 radial sections of the distortion vector field in FIG. 7. Note that a $5^{th}$ order polynomial seems to approximate the errors rather well. You can see the hazards of using a high-order polynomial to try for too close a fit to the measured data: there are large oscillations that would lead to very large errors near the image edges. We must accept higher residuals to achieve better smoothness and fit through the entire image. Note that extrapolation beyond the end-most rows and columns of the grid of calibration points is a problem for grid-based interpolation methods as well.

Other fitting functions, for example, spheroidal harmonic functions.

Study FIG. 8 carefully and use it to help you remember a very important fact:

Small calibration residuals do not mean the map is globally accurate!

We can always find and adjust some function to achieve a good fit between a limited set of points. The proof of accuracy lies in using the calibration on points far away from the calibration set. Find a map that is acceptably good everywhere.

The simplest fitted functions are linear ones. The uncorrected plot in FIG. 7 is a graph of the residuals left over after a full linear correction. Thus we can see that linear maps are not good enough for our purposes. However, I did want to compare different types of linear maps. I did so for the data in FIG. 7, which was taken from a Cosmicar 16 mm lens. This comparison is in Table 1, below.

TABLE 1

Comparison of Different Linear Fits

| Number of Parameters | Description | Maximum Residual, Pixels |
|---|---|---|
| 4 | X and Y Translation, Single Rotation, Single Scale Factor | 4.285 |
| 5 | X and Y Translation, Single Rotation, X and Y Scale Factors | 3.111 |
| 6 | X and Y Translation, X and Y Rotations, X and Y Scale Factor | 3.089 |

The conclusion: accommodating pixel aspect ratio is important for the quality of fit. Skew angle (the difference between 5 and 6 parameters) is not.

For the calibration map I chose a fitted-function map using a polynomial form. Why? I believe that when a good fit can be achieved, a fitted function is better because there is an underlying smooth model of the distortion. This model will probably work well to correct all the points in the image, not just the ones in the calibration set. A fitted function is much less sensitive to a small number of outlier measurement errors. Furthermore, an interpolation scheme provides no independent measure of the quality of the map; all the calibration points can be perfectly fit, leaving no reasonable estimate for the residual errors.

The form of the fitting functions is as follows:

$$x = G_x(u,v) = \sum_{i,j \geq 0}^{i+j \leq n} a_{ij} u^i v^j \quad (7)$$

-continued $$y = G_y(u,v) = \sum_{i,j \geq 0}^{i+j \leq n} b_{ij} u^i v^j \quad (8)$$

where n is the polynomial order.

A calibration can be no more accurate than the raw data used to compute the fitting map. It is essential to provide a high-quality image and high-accuracy feature extraction to get the best calibration.

How do we know the accuracy of a given calibration?. small calibration residuals do not necessarily indicate an accurate calibration. Misunderstanding of the term "accuracy" is so common that we'll start by defining terms.

Calibration residual. The error (Pythagorean distance) between a transformed point and its corresponding known location. The known locations consist of the set of features provided during the computation of the mapping function's parameters. Note that the residuals are different for each map: typically a calibration consists of a transformation from image to physical space Map residual. The error (Pythagorean distance) between a transformed point and its corresponding known location, for any arbitrary point within the domain of the calibration map.

It's my opinion that when we say a calibration is accurate, we mean that its primary map (i.e. the map that transform in the direction we care most about) has low map residuals.

It's important that we have good methods to measure, to an acceptable uncertainty, the residuals that characterize a calibration. The following section describes some methods that I have used as part of this project.

A routine to compute map residuals was implemented. It is intended to support several kinds of characterizations, and so it has some features that are not always needed. This test requires only a single map, but you must have as input a correspondence, that is, a set of matching image points and known corresponding physical locations. The algorithm performs the following steps:

Use the map to transform the observed locations. For an img2phys example:

$$\{x_i',y_i'\}=img2phys \rightarrow \text{transform}(\{u_i,v_i\}) \quad (9)$$

The points $\{x_i',y_i'\}$ are now in physical space. They may or may not be in locations that closely match the given points $\{x_i,y_i\}$, however. Therefore, we usually perform the optional step of performing a least-squares rigid-body fit between the transformed and model points. Then transform the points to fit the model. Following our example:

$$\{x_i'',y_i''\}=T \times \{x_i',y_i'\} \quad (10)$$

where T is the best-fit rigid-body transform between $\{x_i',y_i'\}$ and $\{x_i'',y_i''\}$.

What are we really doing here? Simply removing the restriction that the calibration features be measured in exactly the same locations as they were when the calibration was computed. The rigid-body transform allows us to "move" the calibration plate to a best-fit location over the known plate, so we can check for errors resulting from distortion, not from location. Now we compute the error vectors. For the above example:

$$\{e_{x_i},e_{y_i}\}=\{x_i''-x_i,y_i''-y_i\} \quad (11)$$

Each error vector is simply the coordinate-wise difference between the known point and the point predicted by the map.

To produce the distortion maps in this document, I plotted the error vectors as a function of ideal physical location $\{x_i, y_i\}$. To generate a number indicative of map accuracy, you can also compute statistics of the errors. For example, the maximum map residual is:

$$\text{max-}resid = \max\left(\sqrt{e_{x_i}^2 + e_{y_i}^2}\right) \quad (12)$$

I use the above routine to compute calibration residuals. This provides at least a self-consistency check on the quality of the calibration. In other words, if the calibration residuals are high, you know you have a bad calibration.

The map residual test can also be used to compute an estimate of map residuals, not just calibration residuals. Here are the steps:

Place the calibration plate in the image, and generate a calibration from it. Record the maximum and mean calibration residual.

For each of a number of test cycles, do the following:
Move the calibration plate to a new location within the image.
Acquire the image, and generate a new correspondence from it.
Compute the maximum and mean residual for this new correspondence.

The overall statistics on the residuals from all test cycles can provide you with a reasonable estimate of the map residual error; in other words, the largest error you are likely to encounter in using the calibration. You should also check to see that the residuals during the test cycles are not greatly higher than the calibration residuals. They will naturally be somewhat higher: the calibration was computed precisely to make the calibration residuals as low as possible! But if the map residuals are 50% or more higher, this might indicate that there is something wrong:

The acquired feature locations might be in error, either at calibration time or during the map test.

The form of the calibration function might be a poor match for the distortion of the lens.

To ensure that the calibration map adequately represents the lens distortion, the calibration features should evenly cover the entire image area you intend to use for inspection.

A telecentric lens can be used when scale-induced errors are unacceptably large. A telecentric lens is manufactured to have a single field-of-view size, that does not change with lens-object distance. A theoretically perfect telecentric lens has no scale error at all. It should also almost completely eliminate tilt errors.

What have we learned from this? Measurement accuracy is extremely sensitive to small unmodeled deviations in the device presentation geometry for standard lens setups. For our 16 mm lens we were able to achieve a maximum residual of 0.038 pixels (2.6 microns) at calibration time, but an error of only 100 microns in presentation distance raises this residual to approximately 0.35 pixels (24 microns). We can see from (23) that:

The sensitivity is proportional to O, the center-to-edge distance. Therefore the error is reduced when measuring small devices.

The sensitivity is inversely proportional to f, the focal length. We have already seen how longer focal lengths provide lower residuals (flatter, more distortion-free images). A long focal length also reduces the distance sensitivity.

The sensitivity is proportional to the magnification. Therefore, a larger field of view reduces the distance sensitivity.

Finally, if the required error is smaller than the sensitivity due to unavoidable distance deviations, the use of a telecentric lens should be considered.

We now describe the implementation of a distortion-correcting mathematical transformation of two-dimensional points. This transformation, or map, is polynomial in form. We compute the map by linear least-squares fitting of two corresponding sets of points.

Why is this useful? Principally it is used to correct optical distortion in machine vision systems. FIG. 7 illustrates the errors using a best-fit linear map versus the polynomial map. The largest error for this case (a 16 mm lens) is 2.6 pixels versus 0.038 pixels.

Why a polynomial? Notice how the error vectors in the linear case appear to radiate from a common center. Notice further that the length of the vectors is approximately a function only of radial distance from the center, and not of angle. FIG. 8 shows polynomials fit through one-dimensional cross-sections of the above linear error map. The fit is rather good, suggesting that a two-dimensional polynomial will form a good map.

Fitting a function to a set of data has the advantage of minimizing the sensitivity to measurement errors. Thus if calibrating using an image of a grid of circles, two or three bad circle measurements will have only a small impact on the overall correction map.

Note that in FIG. 8 the use of a high-order polynomial function actually can increase errors by fitting too exactly to the observed data set. Therefore we have limited the polynomial order to five in this implementation.

Using the convention that [x,y] is a model coordinate, and [u,v] is the corresponding observed coordinate, we transform using the following function:

$$x = G_x(u,v) = \sum_{i,j \geq 0}^{i+j \leq n} a_{ij} u^i v^j \quad (13)$$

$$y = G_y(u,v) = \sum_{i,j \geq 0}^{i+j \leq n} b_{ij} u^i v^j \quad (14)$$

where n is the polynomial order. We can see that the total number of coefficients required is:

$$n_c = (n+1)(n+2) \quad (15)$$

For this implementation, we use a single array to hold the coefficients.

Odd members are coefficients for $G_x$ and even members for $G_y$. The full $5^{th}$ order form for $G_x$ and $G_y$ is as follows:

$$\begin{aligned}
G_x(u,v) = & \ a_1 + a_3 u + a_5 v + a_7 u^2 + a_9 v^2 + a_{11} uv + \quad (16)\\
& a_{13} u^3 + a_{15} v^3 + a_{17} u^2 v + a_{19} uv^2 + \\
& a_{21} u^4 + a_{23} v^4 + a_{25} u^2 v^2 + a_{27} u^3 v + a_{29} uv^3 + \\
& a_{31} u^5 + a_{33} v^5 + a_{35} u^3 v^2 + a_{37} u^2 v^3 + a_{39} u^4 v + a_{41} uv^4 \\
G_y(u,v) = & \ a_2 + a_4 u + a_6 v + a_8 u^2 + a_{10} v^2 + a_{12} uv + \quad (17)\\
& a_{14} u^3 + a_{16} v^3 + a_{18} u^2 v + a_{20} uv^2 + \\
& a_{22} u^4 + a_{24} v^4 + a_{26} u^2 v^2 + a_{28} u^3 v + a_{30} uv^3 + \\
& a_{32} u^5 + a_{34} v^5 + a_{36} u^3 v^2 + a_{38} u^2 v^3 + a_{40} u^4 v + a_{42} uv^4
\end{aligned}$$

We solve for $G_x$ and $G_y$ using the Singular Value Decomposition (SVD) technique to solve least-squares problems. We solve the overdetermined equation system:

$$Ax = b \quad (18)$$

that is constructed in the following form (shown for $G_x$ only; the form for $G_y$ is analogous):

$$Ax = b \quad (19)$$

$$\begin{bmatrix} 1 & u_1 & v_1 & u_1^2 & v_1^2 & u_1v_1 & u_1^3 & \ldots \\ 1 & u_2 & v_2 & u_2^2 & v_2^2 & u_2v_2 & u_2^3 & \ldots \\ & & & & \ldots & & & \\ 1 & u_m & v_m & u_m^2 & v_m^2 & u_mv_m & u_m^3 & \ldots \end{bmatrix} \begin{bmatrix} a_1 \\ a_3 \\ a_5 \\ a_7 \\ \ldots \\ a_{41} \end{bmatrix} = \begin{bmatrix} x_1 \\ x_2 \\ \ldots \\ x_m \end{bmatrix}$$

We solve this as follows:

$$x = A^+ b \quad (20)$$

$A^+$ is the pseudo-inverse[1] of A. It has the property that it minimizes:

$$\|Ax - b\| \quad (21)$$

which is just the sum of squared errors in the x coordinates. Note that we can minimize separately in x and y, since each is a separate function of u and v.

[1] Also known as the Moore-Penrose inverse. An excellent treatment is given in:

Strang, Gilbert, *Linear Algebra and Its Applications*, Academic Press, New York, N.Y., 1980.

The traditional method of computing $A^+$ is:

$$A^+ = (A^T A)^{-1} A^T \quad (22)$$

This solves the system when ATA is invertible; however, $A^+$ (as well as a least-squares solution) exists even if not. For this reason we have used the method of SVD to solve for $A^+$; the method also has an excellent reputation for numerical stability and robustness. We have used the implementation given in:

Press, William P., Flannery, Teukolsky, & Vetterling, Numerical Recipes in C. *The Art of Scientific Computing*, Cambridge University Press, Cambridge, UK, 1988.

For any m×n matrix A, where m≥n, A can be written as the product:

$$\begin{array}{cccc} m \times n & m \times n & n \times n & n \times n \\ A & = U & Q & V^T \end{array} \quad (23)$$

$$[\quad] = [\quad] \begin{bmatrix} w_1 & & 0 \\ & \ldots & \\ 0 & & w_n \end{bmatrix} [\quad]$$

where the matrix U is column-orthogonal, i.e.:

$$U^T U = I \quad (24)$$

and the matrix V is orthogonal:

$$V^T V = V V^T = I \quad (25)$$

and the matrix Q is zero except for the non-negative values $w_i$ on its diagonal. The $w_i$ are called the singular values of A.

The SVD is a truly wonderful concoction, and it tells us almost everything we want to know about A. First of all, the pseudo-inverse is obtained by trivially inverting each component:

$$A^+ = V Q^{-1} U^T \quad (26)$$

The number of nonzero singular values is precisely the rank of A. Furthermore, the condition number of A, a measure of its "ill-conditioned-ness", is the ratio of the largest to the smallest singular value.

It is the ability to extract and manipulate the rank of A that makes SVD the proper way to solve our least-squares problem. If the condition number approaches the inverse of the computer's numerical precision, the matrix is numerically, if not theoretically, singular. So before computing (26), we set all sufficiently small $w_i$ to zero.

We used a condition number limit of $10^{11}$ in the implementation of the polynomial fit. Therefore, we set to zero all singular values $w_i < 10^{-11} \cdot w_{max}$.

We found it necessary to scale the matrix A in (19) to reduce its condition number. Columns of A contain successively higher powers of the coordinates, producing a very large dynamic range that could exceed the machine precision.

We encountered this problem fitting from arbitrary model coordinates to image coordinates, the inverse of the typical direction. As we varied the unit of measurement from $10^{-6}$ to $10^6$, the numerical rank changed from 4 to 21 (full rank) to 15, leading to catastrophic loss of accuracy. Naturally we would prefer the fitted solution to be insensitive to the particular unit of measurement chosen. The particular scaling scheme described below completely fixed the problem. In the same test, the scaled A has a condition number of roughly 45 over the full range of unit size, compared with the unscaled condition number that ranged from $10^7$ to $10^{36}$.

The scale factor is computed so that the largest element of A is at most unity. Thus we compute:

$$k = \max(u_i, v_i) \quad (27)$$

and then use in A the scaled elements:

$$\frac{u^i v^j}{k^{i+j}} \quad (28)$$

We can see from the form of (13) and (14) that this scaling simply makes all terms in the polynomial roughly the same order of magnitude. Thus we can add them without catastrophic loss of precision:

$$G_x(u,v) = \sum_{i,j \geq 0}^{i+j \leq n} a_{ij}' \frac{u^i v^j}{k^{i+j}} \quad (29)$$

Once we solve (19), we scale the resulting polynomial coefficients $a_{ij}'$ to reduce the computation required to transform coordinates, as follows:

$$a_{ij} = \frac{a_{ij}'}{k^{i+j}} \quad (30)$$

Let's illustrate this with an example. Suppose we're fitting the following sets of corresponding points:

[12500, 750]   [30, -20]  (31)
[25000, 2100]  [55, -31]
[32000, 2900]  [62, -38]

using the functions $$x = a_1 u + a_2 u^3 v \quad (32)$$
$$y = b_1 v + b_2 u v^3 \quad (33)$$

The x coordinate of the third point would be computed this way:

$$62 = 32000 a_1 + 32000^3 2900 a_2 = 3 \times 10^4 a_1 + 1 \times 10^{17} a_2 \quad (34)$$

We can see that if the linear term contributes 90% of the answer (as is normally the case), $a_1$ must be $10^{14}$ times as large as $a_2$. This is in fact typical, but computing the coefficients with this much dynamic range is intractable. Why? Our A matrix looks like this:

$$A = \begin{bmatrix} u_1 & u_1^3 v_1 \\ u_2 & u_2^3 v_2 \\ u_3 & u_3^3 v_3 \end{bmatrix} = \begin{bmatrix} 12500 & 12500^3 750 \\ 25000 & 25000^3 2100 \\ 32000 & 32000^3 2900 \end{bmatrix} \quad (35)$$

At least in (34) we have the coefficients $a_i$ to scale the terms in the summation to be roughly equal to each other. The large terms are really intended to add a minor "curvature tweak" to the dominant linear terms, yet their magnitude is so large that only two or three significant digits in the linear terms will survive their addition or subtraction. Yet to compute the SVD we must do exactly that: add or subtract linear combinations of columns with each other. Thus we have to scale A to compute $A^+$.

We'll use the maximum coefficient value as a scale factor:

$$k = 32000 \quad (36)$$

Our new A matrix becomes:

$$A = \begin{bmatrix} \frac{12500}{32000} & \frac{12500^3 750}{32000^4} \\ \frac{25000}{32000} & \frac{25000^3 2100}{32000^4} \\ \frac{32000}{32000} & \frac{32000^3 2900}{32000^4} \end{bmatrix} = \begin{bmatrix} 0.39 & 0.0014 \\ 0.78 & 0.031 \\ 1 & 0.091 \end{bmatrix} \quad (37)$$

We have reduced the dynamic range from $10^{13}$ to $10^3$ by scaling! But now, when we solve for the coefficients, we've really solved a different problem; e.g., (34) becomes:

$$62 = \frac{32000}{k} a_1' + \frac{32000^3 2900}{k^4} a_2' \quad (38)$$

We fix this up by changing the form of (38) as follows:

$$62 = \quad (39)$$

$$32000 \left( \frac{a_1'}{k} \right) + 32000^3 2900 \left( \frac{a_2'}{k^4} \right) \equiv a_1 32000 + a_2 32000^3 2900$$

This is how we arrived at the scaling in equations (29) and (30).

For enhanced speed, the image correction calibration map is best implemented as a lookup table, where the surface represented by the polynomial function is approximated by a close-fitting tiled surface. Each of the tiles of the surface is a linearized version of the polynomial function. Increasing the number of the tiles, while decreasing the size of the tiles, provides higher accuracy, but requires more memory. Use of a look up table in this way provides the accuracy of the polynomial fit method, with the speed of the grid interpolation approach.

Returning again to FIG. 6, to estimate a specific local-to-global coordinate transformation for each field of view (50), our knowledge of the relative distances between the landmarks of the calibration targets is now exploited. This knowledge can be obtained knowledge in a variety of ways. For example, the information can be obtained directly from the calibration plate, either by reading information that was printed on the plate in the form of one or more barcodes, as described above, or in some other machine readable form. Or, precise knowledge of the layout of the calibration plate, in conjunction with approximate knowledge of position of a calibration target on the calibration plate, can provide precise knowledge of the relative distance between calibration targets. Alternatively, the relative distance information can be provided by the manufacturer on paper or magnetic media.

Alternatively, the relative distances between the landmarks of the calibration targets can be measured using a machine vision technique, for example.

To estimate the transformation from distortion-corrected camera coordinates into global coordinates (50), for a given pixel in a given field of view, the following procedure is performed. The vector that represents the distortion-corrected distance of a pixel from a landmark in a field of view, is added to the distance of the landmark from an arbitrarily selected origin that is common to all the fields of view. The resulting distance is the distortion-corrected position of the pixel in the global coordinate system.

It should be noted that, theoretically, the order in which the distortion correction transformation and the local-to-global coordinate transformation are performed is significant. This is because the transformations are vector maps, and the combination of the vector maps is not commutative. In particular, the calibration map estimated for the field of view of each camera provides an error correction vector for each pixel in the field of view. Likewise, the local-to-global transformation map for each pixel in each field of view provides an local-to-global coordinate transformation vector. The two transformations can be combined into a single transformation that performs both image distortion correction, and local-to-global coordinate transformation, so that given the identity of any pixel, and the camera that acquired it, we can know the position in the global coordinate system. This position can be the actual physical position in the reference frame of a mechanical device, such as a wafer orientation stage.

However, for purposes of implementation, if image distortion correction and local-to-global coordinate transformation are implemented separately, the order in which they are performed determines their particular implementation, and is therefore important. For example, it is relatively straightforward to generate a look-up table that implements a local image distortion correction transformation for each field of view that is to be applied first to an image, and to generate a look-up table that implements a subsequent local-to global coordinate transformation for each field of view.

In the alternative, although it is theoretically possible, a distorted local-to-distorted global coordinate transform look-up table is relatively inefficient to generate, as it is also difficult to generate a look-up table that implements a global image distortion correction transformation that is to be applied last to each field of view of the distorted global image.

Referring to FIG. 9, at run-time, an image of a different portion of an object is acquired from each of a plurality of cameras (52). The object can be rigidly mounted, such as by using a vacuum chuck, pneumatic toe clamp, or vice, or can be moving rapidly by the cameras, and instantaneously imaged using a strobe light.

Next, feature points of interest, such as points on the perimeter of a semiconductor wafer, are found (54) using any technique for finding features in an image. Next, all of the pixels in each field of view are corrected for camera distortion (56) using the distortion correction maps discussed above. In a preferred embodiment, to improve computational efficiency, only pixels associated with feature points of interest are corrected. Then, the corrected local coordinates of the feature points are transformed into global coordinates (58). The global coordinates can be the real physical coordinates, or other coordinates adapted for further processing.

Other modifications and implementations will occur to those skilled in the art without departing from the spirit and scope of the invention as claimed. Accordingly, the above description is not intended to limit the invention except as indicated in the following claims.

What is claimed is:

1. A method for precisely coordinating multiple fields of view of a plurality of fixed cameras so as to facilitate determining the distance between features each disposed within a different field of view, the method being especially useful when there is image distortion in each field of view, the method comprising the steps of:

at calibration-time, fixing a substantially rigid dimensionally-stable substrate including a plurality of calibration targets each having a reference feature, such that a calibration target is within the field of view of each said camera;

acquiring relative displacement information regarding at least the linear displacement of each said reference feature with respect to at least one other said reference feature;

for each camera, acquiring an image of a calibration target to provide a plurality of acquired calibration target images;

generating an image distortion-correction map for each acquired calibration target image, and at run-time, for each camera, acquiring an image of a portion of said object to provide a plurality of partial object images;

applying said image distortion-correction map to each partial object image to provide a plurality of corrected partial object images; and using said relative displacement information to determine the relative displacement of a first point in a first corrected partial object image with respect to a second point in a second corrected partial object image.

2. The method of claim 1, wherein at run-time, the step of acquiring an image includes acquiring an image from each of at least three cameras.

3. The method of claim 1, further including the step of:

at calibration time, acquiring absolute displacement information regarding at least the linear displacement of at least one said reference feature with respect to a reference feature of a mechanical device.

4. The method of claim 3, wherein said substrate is transparent, and the step of acquiring absolute displacement information includes the step of viewing said reference feature of said mechanical device through said substrate.

5. The method of claim 1, wherein the step of acquiring an image of a calibration target includes the step of acquiring an image of an array of dots.

6. The method of claim 1, wherein the step of acquiring an image of a calibration target includes the step of acquiring the image of a grid of lines.

7. The method of claim 1, wherein the step of acquiring an image of a calibration target includes the step of acquiring an image of two non-parallel lines for indicating an origin of said calibration target.

8. The method of claim 1, wherein said step of acquiring relative displacement information includes acquiring relative angular displacement information.

9. The method of claim 1, wherein said step of generating a distortion-correction map includes the step of determining the coefficients of a polynomial.

10. The method of claim 9, wherein said step of determining the coefficients of a polynomial includes the step of determining the coefficients of a fifth-order polynomial.

11. The method of claim 1, wherein said step of generating a distortion correction map includes the step of precomputing said distortion correction map and storing the results so-computed in a look-up table.

12. The method of claim 1, wherein the step of applying said distortion-correction map includes the step of reading a correction parameter in a look-up table.

13. A method for precisely coordinating multiple fields of view of a plurality of fixed cameras so as to facilitate determining the distance between features each disposed within a different field of view, the method being especially useful when there is image distortion in each field of view, the method comprising the steps of:

at calibration-time, fixing a plurality of cameras with respect to a calibration plate including a plurality of calibration targets;

for each camera, generating an image distortion-correction map;

for each camera, generating a transformation of camera coordinates into global coordinates; and at run-time, for each camera, acquiring an image of a portion of said object to provide a plurality of partial object images;

applying said image distortion-correction map to each partial object image to provide a plurality of corrected partial object images; and using said transformation of camera coordinates into global coordinates to determine the relative displacement of a first feature point in a first corrected partial object image with respect to a second feature point in a second corrected partial object image.

14. The method of claim 13, further including the step of:

at calibration time, acquiring absolute displacement information regarding at least the linear displacement of at least one said reference feature with respect to a reference feature of a mechanical device.

15. The method of claim 13, wherein said step of generating a distortion-correction map includes the step of determining the coefficients of a polynomial.

16. The method of claim 13, wherein said step of generating a distortion correction map includes the step of pre-computing said distortion correction map and storing the results so-computed in a look-up table.

17. A method for precisely coordinating multiple fields of view of a plurality of fixed cameras so as to facilitate determining the distance between features each disposed within a different field of view, the method being especially useful when there is image distortion in each field of view, the method comprising the steps of:

at calibration-time, fixing a plurality of cameras with respect to a calibration plate including a plurality of calibration targets;

for each camera, generating an image distortion-correction map using said plurality of calibration targets;

for each camera, generating a transformation of local camera coordinates into global coordinates using said plurality of calibration targets;

combining said image distortion-correction map and said transformation of local camera coordinates into global coordinates to provide a corrected local-to-global map for determining the distance between features each disposed within a different field of view, even when there is image distortion in each field of view; and at run-time, for each camera, acquiring an image of a portion of said object to provide a plurality of partial object images;

applying said corrected local-to-global map to determine the relative displacement of a first feature point in a first partial object image with respect to a second feature point in a second partial object image.

18. The method of claim 17, further including the step of:

at calibration time, acquiring absolute displacement information with respect to a reference feature of a mechanical device.

19. The method of claim 17, wherein said step of generating an image distortion-correction map includes the step of determining the coefficients of a polynomial.

20. The method of claim 17, wherein said step of generating an image distortion correction map includes the step of pre-computing said image distortion correction map and storing the results so-computed in a look-up table.

* * * * *